(12) United States Patent
Ries et al.

(10) Patent No.: US 11,697,027 B2
(45) Date of Patent: Jul. 11, 2023

(54) CARDIAC PACING DEVICE WITH MECHANICAL MODE SWITCHING

(71) Applicant: Medtronic, Inc., Minneapolis, MN (US)

(72) Inventors: Andrew J. Ries, Lino Lakes, MN (US); Wade M. Demmer, Coon Rapids, MN (US); Troy E. Jackson, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

(21) Appl. No.: 17/028,645

(22) Filed: Sep. 22, 2020

(65) Prior Publication Data

US 2021/0106837 A1 Apr. 15, 2021

Related U.S. Application Data

(60) Provisional application No. 62/913,276, filed on Oct. 10, 2019.

(51) Int. Cl.
*A61N 1/375* (2006.01)

(52) U.S. Cl.
CPC ....... *A61N 1/37512* (2017.08); *A61N 1/3754* (2013.01)

(58) Field of Classification Search
None
See application file for complete search history.

(56) References Cited

U.S. PATENT DOCUMENTS

| 7,231,253 | B2 | 6/2007 | Tidemand et al. |
| 8,364,278 | B2 * | 1/2013 | Pianca .................. H01R 43/16 |
| | | | 600/377 |
| 9,220,902 | B2 | 12/2015 | Ries et al. |
| 9,403,022 | B2 | 8/2016 | Ries et al. |

(Continued)

FOREIGN PATENT DOCUMENTS

| EP | 2540340 A1 | 1/2013 |
| WO | 2007059343 A2 | 5/2007 |

OTHER PUBLICATIONS

"Capsure® VDD-2 5038 Steroid eluting, implantable, fined, bipolar ventricular sensing, and pacing transvenous lead," Technical Manual, Jun. 9, 2014, 14 pp.

(Continued)

*Primary Examiner* — Erica S Lee
(74) *Attorney, Agent, or Firm* — Shumaker & Sieffert, P.A.

(57) ABSTRACT

An implantable medical device includes an electrically conductive first housing, a conductive feedthrough extending through the first housing, electronic circuitry positioned within the first housing, a device electrode, and a second housing. The electronic circuitry is electrically coupled to the first housing and the feedthrough, and senses electrical signals of a patient and/or delivers electrical stimulation therapy to the patient via the first housing and the feedthrough. The device electrode is configured to electrically connect with tissue and/or a fluid at a target site in the patient. A lead connector is configured to connect to a proximal end of an implantable medical lead. The lead connector includes a first connector contact electrically coupled to the feedthrough and a second connector contact electrically coupled to the first housing.

26 Claims, 9 Drawing Sheets

(56) References Cited

U.S. PATENT DOCUMENTS

| | | |
|---|---|---|
| 10,112,045 B2 | 10/2018 | Anderson et al. |
| 2010/0137960 A1 | 6/2010 | Moffitt et al. |
| 2015/0051613 A1* | 2/2015 | Schmidt .............. A61N 1/3756 |
| | | 606/129 |
| 2018/0126161 A1* | 5/2018 | Chin .................... A61N 1/3756 |

OTHER PUBLICATIONS

"Meet Micra," Micra™ Transcatheter Pacing System, Aug. 2016, 5 pp.

"Micra™ Transcatheter Pacing System MC1VR01," Medtronic Product Specifications, Apr. 12, 2016, 8 pp.

International Search Report and Written Opinion of International Application No. PCT/US2020/054697, dated Jan. 14, 2021, 12 pp.

* cited by examiner

CARDIAC PACING DEVICE WITH MECHANICAL MODE SWITCHING

This application claims the benefit of U.S. Provisional Application Ser. No. 62/913,276, filed Oct. 10, 2019, the entire content of which is incorporated herein by reference.

TECHNICAL FIELD

The disclosure relates to cardiac pacing, and more particularly, to cardiac pacing using a pacing device coupled to an implantable lead.

BACKGROUND

An implantable pacemaker may monitor conditions of the patient's heart and may deliver pacing pulses to a patient's heart. In some examples, the implantable pacemaker comprises a pulse generator and one or more electrical leads. The pulse generator may, for example, be implanted in a small pocket in the patient's chest. The electrical leads may be coupled to the pulse generator, which may contain circuitry that generates pacing pulses and/or senses cardiac electrical activity. The electrical leads may extend from the pulse generator to a target site (e.g., an atrium and/or a ventricle of the patient's heart) such that electrodes at the distal ends of the electrical leads are positioned at a target site. The pulse generator may provide electrical stimulation to the target site via the electrodes.

Leadless pacing devices have also been proposed for delivering therapeutic electrical signals to the heart. Such a leadless pacing device may include one or more electrodes on its outer housing to deliver therapeutic electrical signals to the patient's heart. The leadless pacing device may be positioned within or outside of the heart and, in some examples, may be anchored to a wall of the heart via one or more fixation mechanisms. Leadless pacing devices are generally configured for so-called "bipolar pacing," which refers to configurations in which both electrodes (cathode and anode) are positioned inside or are directly affixed to the patient's heart, with the heart muscle and/or intraventricular blood completing the bipolar circuit.

SUMMARY

The disclosure describes implantable cardiac pacing devices that are selectively configurable in a bipolar pacing and sensing configuration or a unipolar pacing and sensing configuration. In a unipolar configuration, one electrode is positioned inside or directly affixed to the heart, and the other electrode is positioned at some distance from the heart, thereby including a greater amount of tissue and body fluid in the electrical path of field for pacing or sensing than in the case of a bipolar configuration. The cardiac pacing devices of this disclosure are configured to enable a clinician to select between the unipolar and bipolar configurations at the time of implantation, without requiring the clinician to reconfigure the circuitry of the cardiac pacing device. Rather, the cardiac pacing devices of this disclosure are configured to permit selection between the unipolar and bipolar configurations by way of a mechanical or structural modification prior to implantation and activation in the patient's body.

To implement a unipolar cardiac pacing mode, for example, the designs of this disclosure leverage devices that are otherwise used for leadless, bipolar cardiac pacing, by directly exposing an electrically conductive housing to the electrically conductive tissue and/or electrically conductive body fluid of the patient, thereby enabling current to flow to another electrically conductive component deployed to the target site, such as the patient's heart, with the pacing circuit being completed by a unipolar pacing lead. To implement a bipolar cardiac pacing mode, the designs of this disclosure maintain full enclosure of the bipolar cardiac pacing component within an electrically insulative housing, and complete the pacing circuit via a bipolar lead that connects to two points of the bipolar pacing device, through connector contacts disposed on the electrically insulative outer housing.

The pacing devices of this disclosure include a removable portion, e.g., a plug, a cover, a lid, etc. that the clinician can affix to or detach from an opening in the outer, electrically insulative housing of the cardiac pacing device. When present, the plug covers a device electrode positioned on or electrically connected to the electrically conductive inner housing, thereby enabling the bipolar pacing mode via the bipolar lead. When the plug is removed, the opening in the outer electrically insulative housing exposes the device electrode, thereby enabling the unipolar pacing mode by way of a pacing circuit formed by the patient's tissue and/or body fluid in combination with the unipolar pacing lead coupled to a single lead connector that connects to the inner electrically conductive housing, e.g., connects to a feedthrough pin through the inner electrically conductive housing, through the outer electrically insulative housing.

In one aspect, the disclosure is directed to an implantable medical device (IMD). The IMD includes a first housing, the first housing being electrically conductive, a feedthrough that extends through the first housing, the feedthrough being electrically conductive, electronic circuitry positioned within the first housing, a device electrode, and a second housing that encloses the first housing, the feedthrough, and the device electrode. The electronic circuitry is electrically coupled to the first housing and the feedthrough, and the electronic circuitry is configured to sense electrical signals of a patient and/or deliver electrical stimulation therapy to the patient via the first housing and the feedthrough. The device electrode either includes at least a portion of the first housing or is electrically coupled to the first housing, and the device electrode is configured to electrically connect with tissue and/or a fluid at a target site in a patient. The second housing includes a lead connector and a removable portion. The lead connector is configured to connect to a proximal end of an implantable medical lead. The lead connector includes a first connector contact electrically coupled to the feedthrough and a second connector contact electrically coupled to the first housing. When present, the removable portion of the second housing covers the device electrode, thereby enabling a bipolar pacing mode. When the removable portion is removed, the defined opening exposes the device electrode, thereby enabling a unipolar pacing mode (e.g., when coupled with a unipolar pacing lead).

In another aspect, the disclosure is directed to an IMD that includes a subassembly. The subassembly includes a first housing, the first housing being elongated, substantially sealed, and electrically conductive. The IMD also includes a feedthrough that extends through a distal end of the first housing, the feedthrough being electrically conductive feedthrough. The IMD includes electronic circuitry within the first housing. The electronic circuitry is configured to at least one of sense electrical signals of a patient or deliver electrical stimulation therapy to the patient via the first housing and the feedthrough. The subassembly also includes a device electrode that includes at least a portion of the first housing or is electrically coupled to the first housing. The IMD includes a second housing enclosing the subassembly and the device electrode. The second housing includes a removable portion and a lead connector configured to connect to a proximal end of an implantable medical lead, the lead connector including first and second connector contacts, where the removable portion, when present, covers the device electrode thereby insulating the device electrode from at least one of a fluid or tissue at a target site in a patient, and when removed, exposes the device electrode thereby enabling conduction between the device electrode and the at least one of the fluid or the tissue at the target site in the patient.

In another aspect, disclosure is directed to an IMD kit that includes an IMD and a removable plug. The IMD includes a subassembly and a second housing. The subassembly includes a first housing that is elongated, substantially sealed, and electrically. The IMD also includes a feedthrough that extends through a distal end of the first housing, the feedthrough being electrically coupled to the electronic circuitry. The IMD includes electronic circuitry enclosed within and electrically coupled to the first housing, the electronic circuitry configured to at least one of generate an electrical stimulation therapy for delivery to a patient and monitor a physiological parameter of the patient. The subassembly also includes a device electrode electrically coupled to the electronic circuitry. The second housing encloses the subassembly and the device electrode, and defines a first opening adjacent the device electrode. The second housing includes a lead connector configured to connect to a proximal end of an implantable medical lead, the lead connector including a first connector contact electrically coupled to the feedthrough and a second connector contact electrically coupled to the electronic circuitry. The removable plug is configured to be inserted into the first opening of the second housing. The removable plug, when inserted into the first opening of the second housing, covers the device electrode thereby insulating the device electrode from at least one of a fluid and tissue at a target site in a patient, and when removed from the first opening of the second housing, exposes the device electrode thereby enabling conduction between the device electrode and the at least one of the fluid or tissue at the target site in the patient. The removable plug (or cover, lid, tear-off covering, etc.) may be installed during manufacture and removed only when the clinician determines that unipolar pacing is preferred.

In another aspect, disclosure is directed to a method for configuring an IMD prior to implantation in a patient. The method includes making a pacing determination to provide one of bipolar pacing and unipolar pacing with the IMD. The IMD includes electronic circuitry configured to provide a bipolar pacing mode and a unipolar pacing mode, first housing that is electrically conductive and encloses and is electrically coupled to the electronic circuitry, a feedthrough that extends through the first housing and is electrically coupled to the electronic circuitry, a device electrode electrically coupled to the electronic circuitry, and a second housing enclosing the first housing, the feedthrough, and the device electrode. The second housing includes a first portion defining a opening adjacent the device electrode, a removable portion, and a lead connector including a first connector contact electrically coupled to the feedthrough and a second connector contact electrically coupled to the electronic circuitry. The method further includes selecting one of a bipolar implantable medical lead or a unipolar implantable medical lead based on the pacing determination, and inserting a proximal end of the selected implantable medical lead into the lead connector. The method further includes configuring the removable portion of the second housing based on the pacing determination.

In another aspect, the disclosure is directed to a computer-readable storage medium including computer-readable instructions for execution by a processor. The instructions cause a programmable processor to perform any whole or part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable medium is an article of manufacture and is non-transitory.

The cardiac pacing devices of this disclosure provide several technical improvements over existing cardiac pacing technology. By enabling the clinician to configure the cardiac pacing device to provide either bipolar or unipolar pacing and sensing at the time of implantation, the cardiac pacing device designs of this disclosure make the benefits of both bipolar and unipolar pacing and sensing available for a given patient, while using a simplified device and allowing for mechanical reconfiguration. Moreover, the designs of this disclosure, by effecting the selection between bipolar and unipolar pacing and sensing modes, respectively, via the placement or removal of the plug on/from the outer housing, enable the clinician to configure the cardiac pacing device in a fast and easy way, and in the sterile environment in which the implantation procedure is performed without the aid of a programming device. Additionally, due to the mechanical configurability of the pacing devices of this disclosure, such devices may not need to include circuitry for electrically switching between bipolar and unipolar modes, which could increase the size and/or complexity of the devices.

The details of one or more examples are set forth in the accompanying drawings and in the description below. Other features, objects, and advantages will be apparent from the description and drawings, and from the claims.

DETAILED DESCRIPTION

Cardiac pacing devices of this disclosure may be implanted in a pocket within a patient's chest, and can be coupled to either a bipolar pacing lead or a unipolar pacing lead. A clinician may choose between the bipolar lead and the unipolar pacing lead at the time of implantation, based on various factors observed at or before the time at which the implantation procedure is performed. That is, the clinician may select between bipolar and unipolar pacing and sensing for the patient, based on which of these two modes the clinician determines to be better suited to the patient's needs.

The cardiac pacing device of this disclosure is designed to enable the selection between bipolar and unipolar modes at the time of implantation via mechanical manipulation. As discussed above, the clinician can affix either a bipolar lead or a unipolar lead to the cardiac pacing device just before implantation. The device designs of this disclosure enable the clinician to dynamically configure the cardiac pacing device to operate in conformance with either the bipolar lead or the unipolar lead, as part of the implantation procedure.

Layered or "nested" designs of this disclosure include an electrically conductive inner housing encased within an electrically insulative outer housing. The electrically insulative outer housing of this disclosure includes an opening and a plug that can be affixed to or removed from the opening. When removed, the plug exposes the electrically conductive inner housing to the body of the patient, and can complete a unipolar pacing or sensing circuit with the unipolar lead via the tissue and/or body fluid of the patient. When affixed, the plug blocks direct contact between the electrically conductive inner housing and the body of the patient, thereby maintaining the electrically insulative property of the outer housing, and enabling completion of the bipolar pacing and sensing circuit via the bipolar lead's two points of direct contact with the cardiac pacing device.

During the implantation procedure, the clinician can either affix or detach the plug from the opening in the electrically insulative outer housing, to dynamically change the pacing lead compatibility of the cardiac pacing device between bipolar and unipolar compatibilities. By enabling pacing and sensing mode toggling via a mechanical manipulation (e.g., the affixation or removal of the plug), the cardiac pacing devices of this disclosure can be reconfigured easily at the time of implantation, within the operating environment, without the need to delay the implantation procedure or to remove the cardiac pacing device from the operating room for other types of manipulation. In this way, the cardiac pacing devices of this disclosure enable the clinician to avail of the potential benefits of both bipolar and unipolar modes, without requiring a decision far in advance of the implantation procedure.

Figure 1:
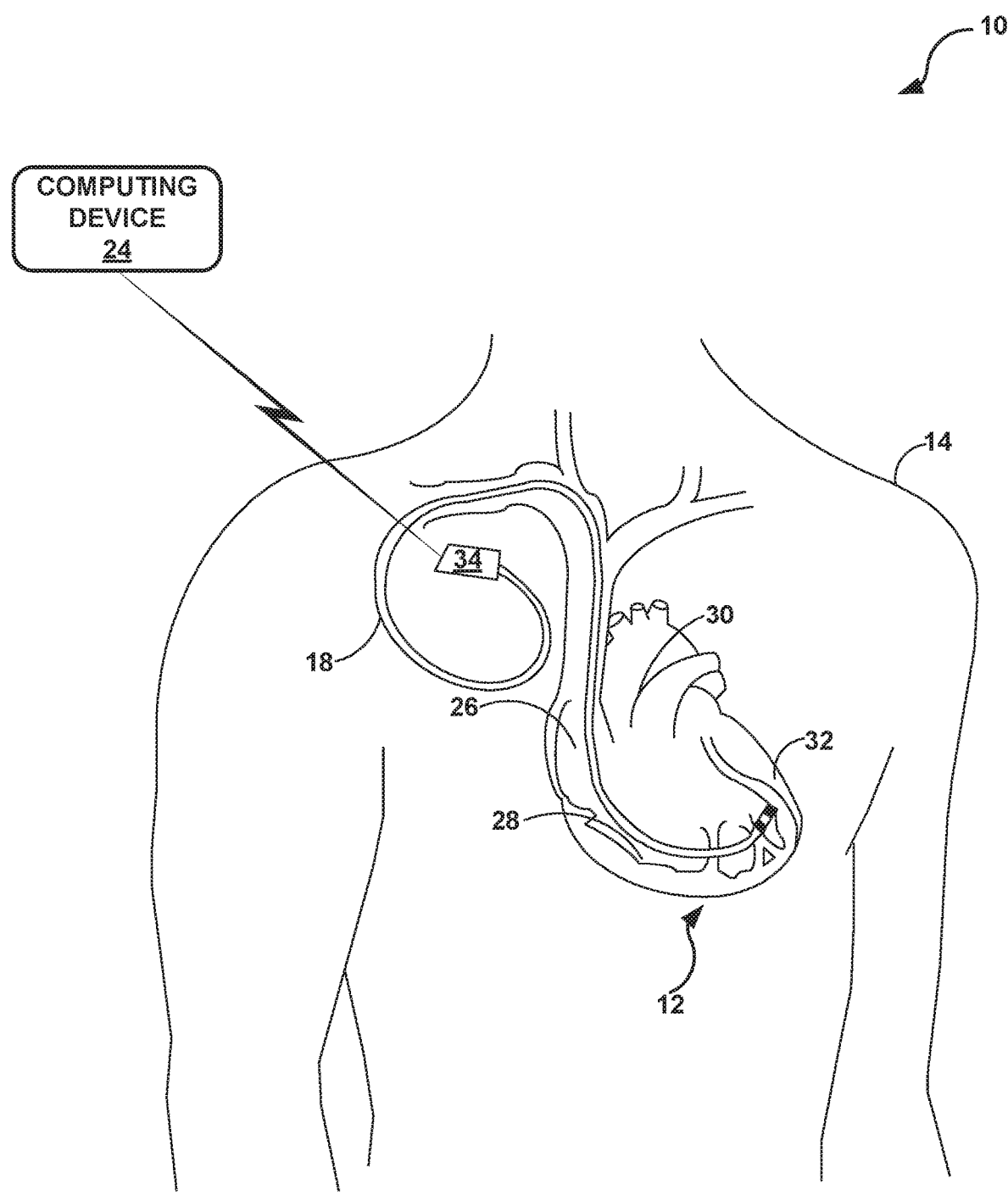
FIG. 1 is a diagram illustrating an example therapy system that may be used to monitor one or more physiological parameters of a patient and/or to provide therapy to the heart of the patient.

FIG. 1 is a diagram illustrating an example therapy system 10 that may be used to monitor one or more physiological parameters of a patient 14 and/or to provide therapy to the heart 12 of patient 14. Therapy system 10 includes IMD 34, which is coupled to a lead 18, and to computing device 24. At some instances in this disclosure, each of IMD 34 and lead 18 may be referred to generally as an IMD. In some examples, IMD 34 may be an implantable pacemaker (e.g., a cardiac pacing device) that delivers electrical signals to heart 12 via electrodes coupled to lead 18. IMD 34 is one example of an electrical therapy generator, and is configured for attachment to the proximal end of lead 18. In other examples, in addition to (or instead of) pacing therapy, IMD 34 may deliver neurostimulation signals to target sites on or in heart 12, or at other locations within patient 14. In other examples, IMD 34 may not provide any stimulation functionalities and, instead, may be a dedicated monitoring device.

Patient 14 represents a human patient in FIG. 1, although it will be appreciated that system designs of this disclosure may be applicable to pacing and/or monitoring devices used in certain non-human patients as well. Lead 18 extends into heart 12 of patient 14, and lead 18 delivers electrical stimulation to heart 12 and/or senses electrical activity of heart 12.

In the example illustrated by FIG. 1, lead 18 is a right ventricular (RV) lead that extends through one or more veins (not shown), the superior vena cava (not shown), right atrium 26, and into right ventricle 28. Lead 18 may deliver RV pacing to heart 12. In another example, lead 18 may be a left ventricular (LV) lead that extends through one or more veins, the vena cava, right atrium 26, and into the coronary sinus 30, to a region adjacent to the free wall of left ventricle 32 of heart 12. In such examples, lead 18 may deliver LV pacing to heart 12. In another example still, lead 18 is a right atrial (RA) lead that extends through one or more veins and the vena cava, and into the right atrium 26 of heart 12. In such examples, lead 18 may deliver RA pacing to heart 12. While shown in FIG. 1 as being implanted in the pectoral region of patient 14, it will be appreciated that, in other examples, IMD 34 may be implanted at other locations, such in the abdominal region of patient 14, etc. Also, while lead 18 is shown as extending into right ventricle 28, it will be appreciated that in other examples, lead 18 may contact other areas, such as an epicardial region of patient 14.

IMD 34 may sense electrical signals attendant to the depolarization and repolarization of heart 12 via one or more electrodes coupled to lead 18. IMD 34 provides pacing pulses to heart 12 based on these sensed electrical signals. The configurations of electrodes used by IMD 34 for sensing and pacing may be unipolar or bipolar, depending on whether lead 18 is a unipolar lead or is a bipolar lead.

Computing device 24 may be used to communicate with IMD 34. For example, a user may use computing device 24 to retrieve information from IMD 34 regarding the performance or integrity of lead 18, and may interact with computing device 24 to program, e.g., select parameters for, therapies and sensing provided by IMD 34. Lead 18 may be electrically coupled to a signal generator and a sensing module of IMD 34. In some examples, a proximal end of lead 18 may include one or more electrical contacts that electrically couple to respective electrical contacts within a lead connector of IMD 34.

Again, lead 18 may represent a bipolar lead or a unipolar lead, and in accordance with the designs of this disclosure, the clinician implanting IMD 34 in patient 14 may select between the bipolar and unipolar implementations at the time of the implantation procedure. In accordance with aspects of this disclosure, IMD 34 is constructed in an encapsulated manner, with an outer housing of IMD 34 having an opening that can be covered or exposed, respectively, based on the presence or removal of a removable portion of the outer housing. The outer housing of IMD 34 is constructed of an electrically insulative material. If the clinician affixes the removable portion to the outer housing of IMD 34, the clinician may select a bipolar lead to use as lead 18. Conversely, if the clinician detaches the removable portion from the outer housing of IMD 34, the clinician may select a unipolar lead to use as lead 18.

More specifically, the electrically insulative outer housing may encapsulate or enclose an electrically conductive inner housing. The inner housing may represent the surface of a pacing component (e.g., a component that itself could be otherwise deployed as a pacing device) that is inherently a unipolar electrode when positioned distally from heart 12. If the clinician detaches the removable portion from the outer housing of IMD 34, the electrically conductive inner housing is exposed to the tissue and/or body fluid of patient 14. In this scenario, the exposed inner housing of IMD 34 completes the circuit, via the conductive tissue and/or fluid, with the unipolar electrode of lead 18.

In this way, IMD 34 is structured, according to aspects of this disclosure, to permit the clinician who performs the implantation procedure to dynamically configure IMD 34 mechanically for either bipolar or unipolar pacing and sensing during the implantation procedure, without the need to provide different models of IMD or circuitry within IMD 34 or to require programmable configuration for either bipolar or unipolar pacing and sensing, or to remove IMD 34 from the sterile field or operating room for reconfiguration. Rather, according to aspects of this disclosure, IMD 34 is constructed to permit the clinician to, during the implantation procedure, either (i) affix (or leave in place, as the case may be) the removable portion to the outer housing and attach a bipolar lead as lead 18, thereby configuring IMD 34 for bipolar pacing and sensing, or (ii) detach the removable portion to the outer housing and attach a unipolar lead as lead 18, thereby configuring IMD 34 for unipolar pacing and sensing. By permitting dynamic configuration during the implantation procedure by way of an easy mechanical manipulation, IMD 34 enables the clinician, in procedure, to avail of the benefits of either bipolar or unipolar pacing based on an evaluation of the needs of patient 14.

Figure 2A:
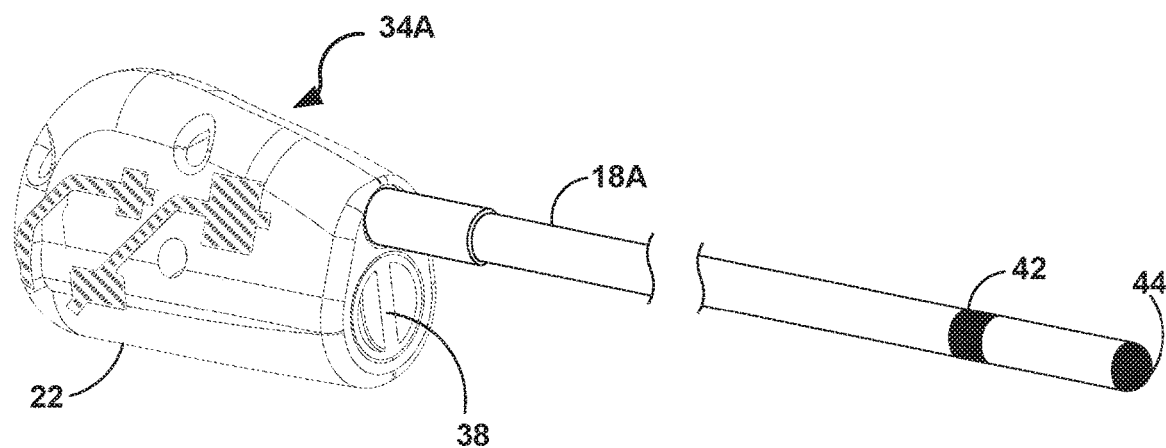
FIGS. 2A & 2B are diagrams illustrating aspects of the implantable medical device (IMD) of FIG. 1 when configured for bipolar pacing and for unipolar pacing, respectively.
Figure 2B:
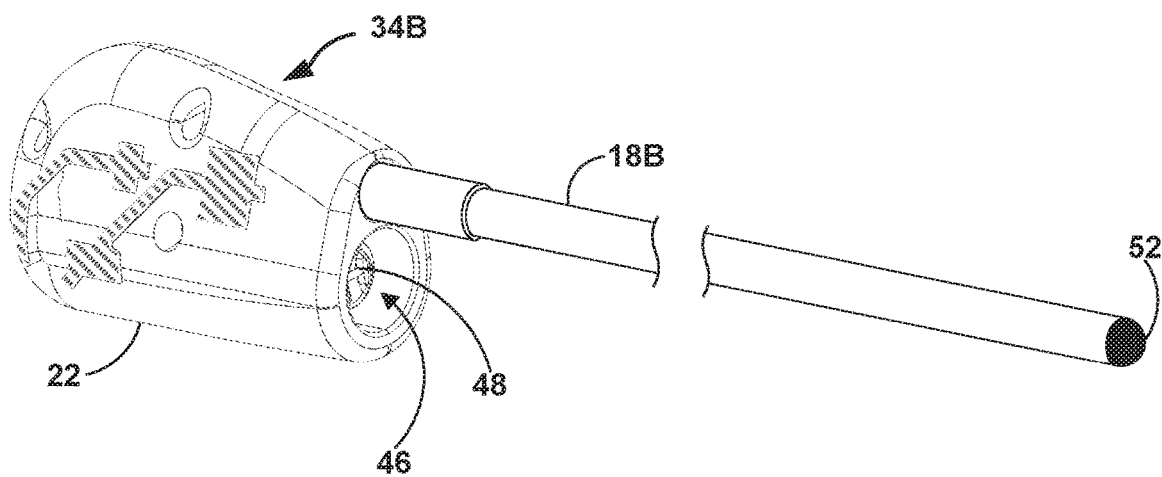

FIGS. 2A and 2B are conceptual diagrams illustrating aspects of IMD 34 when configured for bipolar pacing and for unipolar pacing, respectively. FIG. 2A illustrates IMD 34A, which represents a scenario in which IMD 34 of FIG. 1 is configured to deliver bipolar pacing to heart 12. IMD 34A includes an electrically insulative outer housing 22 and an electrically insulative plug 38. Plug 38 is described herein as representing a "removable portion" of outer housing 22. Plug 38 is configured to seal an opening defined in outer housing 22. IMD 34A is coupled to bipolar lead 18A, which represents a bipolar pacing and sensing capable example of lead 18 illustrated in FIG. 1. Bipolar pacing lead 18A includes electrodes 42 and 44. Plug 38 is also referred to as a "removable plug" in this disclosure.

Plug 38, when affixed to outer housing 22, is configured to form a substantially watertight and/or substantially airtight seal over an opening defined in outer housing 22. In some examples, plug 38 may be inserted into the opening defined in outer housing 22 to form a flush seal. For instance, plug 38 may be inserted into the defined opening such that plug 38 is fastened within the defined opening with a friction fit (also referred to as an interference fit or a press fit). According to designs of this disclosure, both outer housing 22 and plug 38 may be sized and constructed of material that is sufficiently malleable or elastic for the friction fit to provide a tightness level that prevents body fluid of patient 14 to cross through into the enclosure provided by outer housing 22 with plug 38 present. In other examples, plug 38 and the inner surface of the opening of outer housing 22 may be equipped with complementary threads. In these examples, plug 38 covers the opening defined in outer housing 22 by way of being screwed onto the inner surface of the opening defined in outer housing 22.

It will be appreciated that plug 38 is only one non-limiting example of a removable portion of outer housing 22 that the clinician may remove to enable unipolar pacing/sensing, and that other types of removable portions of outer housing 22 are also consistent with the designs of this disclosure. For instance, outer housing 22 may include packaging that covers opening 46 and is attached to the inner rim of opening 46 in a partially perforated manner. The perforation may provide a watertight (or potentially even airtight) seal over opening 46, but may provide a structural feature by which the clinician can remove the packaging using a pull-away or tearing motion. Other examples of removable portions (e.g., with partially/fully cut or otherwise weakened sections enabling removal by force) that the clinician can remove from outer housing 22 to enable unipolar pacing/sensing are also consistent with the designs of this disclosure.

Again, FIG. 2A illustrates a scenario in which IMD 34A is configured to deliver bipolar pacing to heart 12 of patient 14. By virtue of its affixation to outer housing 22, plug 38 blocks (e.g., fully obstructs) the defined opening, and thereby making outer housing 22 a true and full enclosure. In the example IMD 34A, plug 38 fully blocks direct contact between the tissue/body fluid of patient 14 and a device electrode of an inner housing enclosed within the outer housing.

Because the entire outer surface of IMD 34A is electrically insulative, bipolar lead 18A represents the only electrically conductive component illustrated in FIG. 2A. Bipolar lead 18A forms a completed pacing circuit using electrodes 42 and 44, one of which represents an anode and the other of which represents a cathode. Electronic circuitry positioned within outer housing 22 may operate bipolar lead 18A, such as by delivering pacing signals using electrodes 42 and 44. In some examples, the electronic circuitry of IMD 34A may sense electrical signals of patient 14 (e.g., electrical signals representing a cardiac signal output by heart 12) via bipolar lead 18A. In some examples, the electronic circuitry of IMD 34A may deliver electrical stimulation therapy (whether in the form of pacing signals, neurostimulation, or other forms) to patient 14 via bipolar lead 18A.

FIG. 2B illustrates IMD 34B, which represents a scenario in which IMD 34 of FIG. 1 is configured to deliver unipolar pacing to heart 12. IMD 34B includes an electrically insulative outer housing 22. Outer housing 22, in turn, defines opening 46. In one use case scenario, IMD 34B represents IMD 34A, with plug 38 removed, thereby exposing the inner enclosure of outer housing 22. IMD 34B is coupled to unipolar lead 18B, which represents a unipolar pacing and sensing capable example of lead 18 illustrated in FIG. 1. Unipolar lead 18B includes a single electrode, namely, lead electrode 52.

Outer housing 22 defines opening 46 in the example of IMD 34B of FIG. 2B. Opening 46 is not sealed in the case of IMD 34B, in contrast to IMD 34A of FIG. 2A, in which the affixation of plug 38 forms a substantially watertight or potentially even airtight seal. Opening 46 exposes device electrode 48, which is part of a pacing device encased within outer housing 22. The pacing device encased within outer housing 22 is configured to deliver unipolar pacing by using device electrode 48 as a distal electrode in combination with a proximal electrode positioned at the target site or more proximal to the target site than distal electrode 48 is placed.

IMD 34B is connected to unipolar lead 18B in the example shown in FIG. 2B. Unipolar lead 18B includes lead electrode 52, which may be deployed inside or on a chamber of heart 12. Because device electrode 48 is exposed to the body of patient 14 in the construction shown in FIG. 2B, device electrode 48 and lead electrode 52 may complete the pacing and sensing circuit using the electrically conductive tissues and body fluids of patient 14. In some examples, device electrode 48 may be configured to function as an anode, and lead electrode 52 may be configured to function as a cathode of the pacing circuit.

Electronic circuitry of the pacing device encased within outer housing 22 may deliver pacing signals using device electrode 48 and lead electrode 52, by driving a current between the electrodes. In some examples, the electronic circuitry of IMD 34B may sense electrical signals of patient 14 (e.g., electrical signals representing a cardiac signal output by heart 12) via unipolar lead 18B. In some examples, the electronic circuitry of IMD 34B may deliver electrical stimulation therapy (whether in the form of pacing signals, neurostimulation, or other forms) to patient 14 via the circuit formed by device electrode 52 and lead electrode 52.

Figure 3:
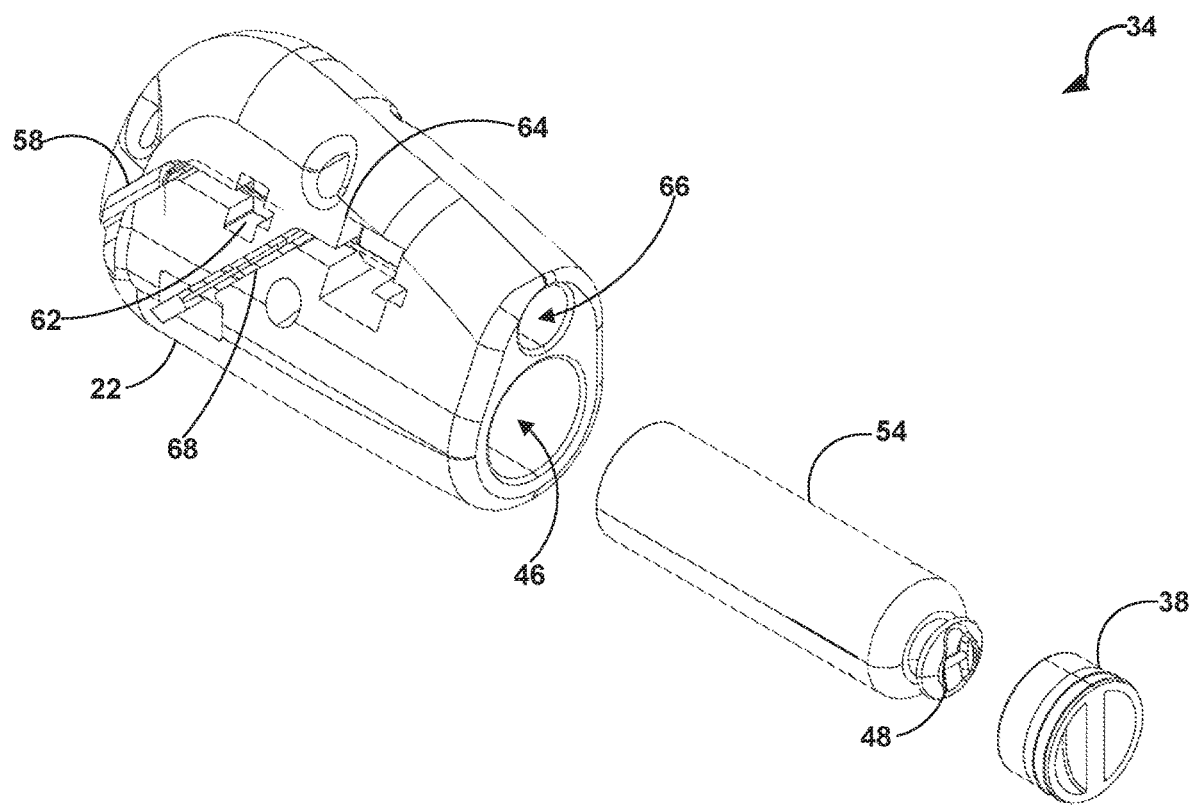
FIG. 3 is a diagram illustrating the IMD of FIG. 1 at a pre-assembly phase.

FIG. 3 is a diagram illustrating IMD 34 at a pre-assembly phase. FIG. 3 may also be described as an exploded view or disassembled view of IMD 34 prior to outer housing 22 being finalized as a fully insulative body. FIG. 3 illustrates outer housing 22 with plug 38 removed, and prior to the enclosure and attachment of the inner housing described above. Inner housing 54 of FIG. 3 is constructed has an electrically conductive exterior and includes or otherwise coupled to device electrode 48. Electronic circuitry positioned within inner housing 54 is configured to drive cardiac pacing signals to heart 12, to sense a cardiac signal output by heart 12, or both. As such, inner housing 22 (including device electrode 48, the electronic circuitry described above, etc.) itself may represent a pacing device. In one non-limiting example, inner housing 22 may take the form of a Micra™ transcatheter pacing system (TPS) available from Medtronic plc, of Dublin, Ireland, which may be modified. Modification of the Micra™ TPS may include, for example, removal of fixation members and a distal header assembly.

Inner housing 54 is described herein as a component that, if deployed in exposed fashion, would deliver unipolar pacing when coupled to a unipolar lead. According to aspects of this disclosure, outer housing 22 is configured to receive inner housing 54 via opening 46. The assembly process of IMD 34 may include the insertion of inner housing 54 into opening 46, and in some examples, the affixation of inner housing 54 to the inside surface of outer housing 22 to enable electrical signal conduction, such as by welding, riveting, or soldering at one or more contact points.

Outer housing 22 also defines connector contacts 62 and 64. Connector contacts 62 enable outer housing to form at least one, and at most two electrical contact points with lead 18, depending on whether lead 18 is a unipolar lead or a bipolar lead. Outer housing 22 is also designed to enable electrical signal communication between inner housing 54 and lead 18 by using one or both of connector contacts 62 and 64 as conduits. Because connector contacts 62 and 64 collectively enable outer housing 22 to couple to lead 18, connector contacts 62 and 64 are described herein as being components of a "lead connector" of outer housing 22.

In the design shown in FIG. 3, outer housing 22 defines a second opening that is an entry/exit point to lead slot 66, in addition to opening 46 that receives inner housing 54. The circumference of lead slot 66 in outer housing 22 enables a friction fit of lead 18 such that lead opening 66 is sealed in a watertight (or potentially airtight) manner upon full insertion of lead 18. Lead slot 66 has a depth and angle within outer housing 22 such that a proximal connector of lead 18 makes contact with connector contact 62 within outer housing 22. In instances in which lead 18 is a bipolar lead, a second proximal connector of lead 18 makes contact with connector contact 64 within outer housing 22, once lead 18 is fully inserted into lead slot 66.

Connector contact 62 is coupled to conduction path 58, and connector contact 64 is coupled to conduction path 68. Conduction paths 58 and 68 electrically couple connector contacts 62 and 64, respectively, to points within outer housing 22. For instance, conduction path 68 may electrically couple connector contact 64 to a portion of the inner surface of outer housing 22 that forms an electrically conductive contact with the body of inner housing 54. In this way, conduction path 68 forms an electrical connection between the body of inner housing 54 and connector contact 64, thereby enabling electrical signal transmission between the body of inner housing 54 and a second proximal connector of lead 18, in instances in which lead 18 is a bipolar lead equipped with two proximal connectors.

If lead 18 is a unipolar lead, then conduction path 68 may remain inactive, because lead 18 may not be equipped with the second proximal connector that conducts electrical signals received at connector contact. Conduction path 58 electrically couples connector contact 62 to a feedthrough pin that is positioned distally from device electrode 48 on inner housing 54. Regardless of whether lead 18 is a bipolar lead or a unipolar lead, conduction path 58 provides signal transmission between the first proximal contact of lead 18 and the feedthrough pin of inner housing 54. Aspects of inner housing 54 are described below in greater detail.

After inner housing 54 is inserted into opening 46 and affixed to the inner surface of outer housing 22, the assembly process of IMD 34 may involve coating the outside surface of outer housing 22 in an insulative material, to contain the conductive properties of conduction paths 58 and 68 within the confines of IMD 34, and to maintain the electrically insulative property throughout the outer surface of outer housing 22. In FIGS. 2A and 2B, conduction paths 58 and 68 are shown with different shading than in FIG. 3, to indicate the differences between post- and pre-assembly properties of conduction paths 58 and 68.

Figure 4:
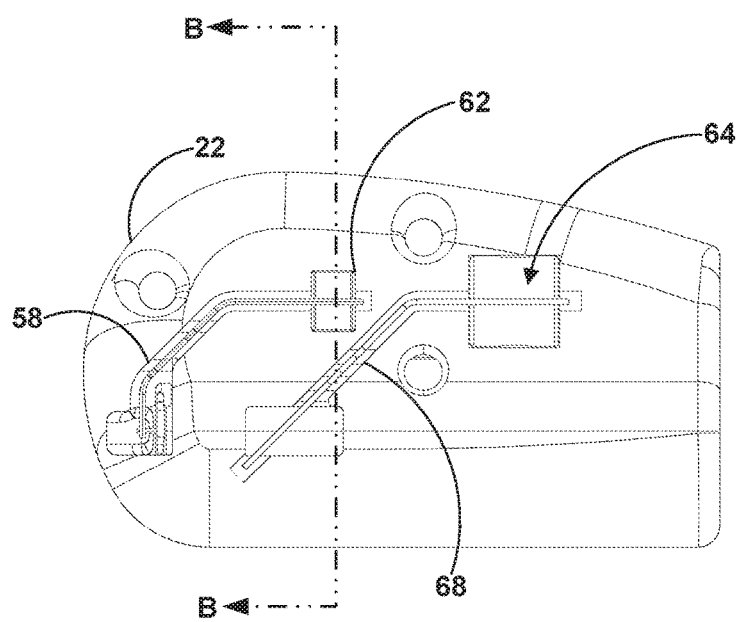
FIG. 4 is a diagram illustrating an outer housing of the IMD of FIG. 1 during the pre-assembly phase of the IMD.

FIG. 4 is a diagram illustrating outer housing 22 during a pre-assembly phase of IMD 34. FIG. 4 provides a side view of outer housing 22 prior to outer housing 22 being finalized as a fully insulative body during the assembly process of IMD 34. As in the case of FIG. 3, conduction paths 58 and 68 are shown in FIG. 4 at a stage prior to being coated with an electrically insulative seal. The B-B line of FIG. 4 illustrates a side view of a plane that forms the basis of a cross-sectional view of outer housing 22 that is described below with respect to FIG. 5.

Figure 5:
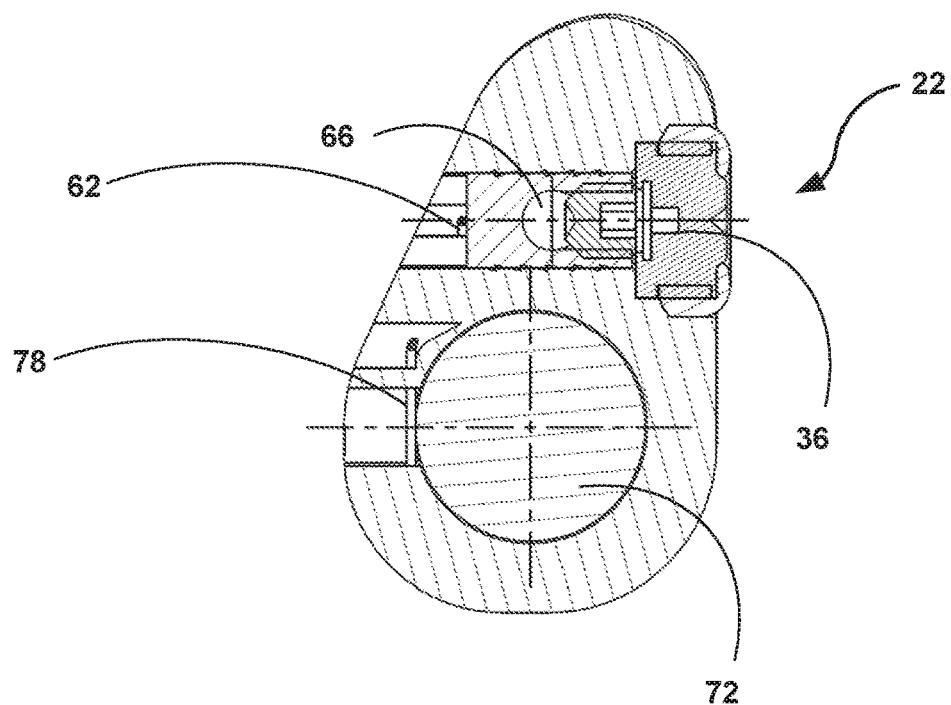
FIG. 5 is a conceptual diagram illustrating a transverse cross-sectional view of an outer housing of the IMD of this disclosure.

FIG. 5 is a conceptual diagram illustrating a transverse cross-sectional view of outer housing 22. FIG. 5 shows chamber 72, which represents a hollow inner portion of outer housing 22. Chamber 72 is configured to hold inner housing 54 which, as described above, represents a component or device that includes electronic circuitry configured to drive pacing signals or to perform cardiac signal sensing functionalities. Opening 46 illustrated in FIG. 2A represents an entry point into chamber 72. Both of opening 46 and the remainder of chamber 72 have a circumference that is sufficiently large to receive inner housing 54. Chamber 72 also has a depth that is sufficiently long to enclose inner housing 54, both when plug 38 is affixed to opening 46 as well as when opening 46 is left unobstructed. Inner housing 54 may be affixed to an outer rim of chamber 72 in such a way that electrical signals can be conducted via the affixation mechanisms, such as with welds, with rivets, or with soldered connections at one or more contact points.

FIG. 5 also illustrates set screw 36, which is part of an example of an affixation mechanism by which a proximal contact of lead 18 is mechanically and electrically connected to connector contact 62 of outer housing 22. The affixation mechanism may or may not include additional set screws other than set screw 36, in various implementations. In other examples, the proximal contact of lead 18 may be mechanically and electrically connected to connector contact 62 by way of connector blocks, contacts, connection pins, snap connectors, or another suitable mechanical and electrical coupling mechanism that permits electrical signal propagation between the proximate contact of lead 18 and connector contact 62. FIG. 5 also illustrates internal contact 78 that internally connects connector contact 62 to components of inner housing 54. Aspects of internal contact 78 will be described below in greater detail, with respect to FIG. 7.

Figure 6:
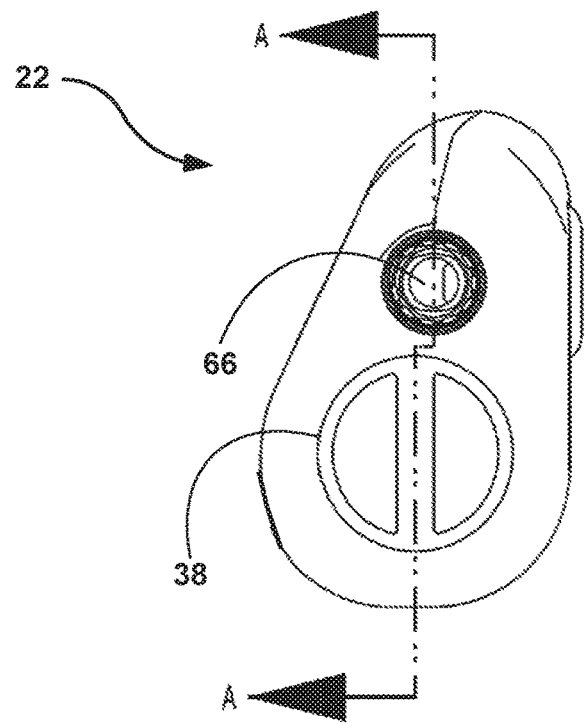
FIG. 6 is a conceptual diagram illustrating an elevation view of a proximal end of the outer housing of the IMD of this disclosure.

FIG. 6 is a conceptual diagram illustrating an elevation view of a proximal end of outer housing 22. FIG. 6 illustrates an example in which IMD 34 is configured to perform bipolar pacing and/or sensing, as shown by the presence of plug 38. The clinician may affix bipolar lead 18A to outer housing 22. That is, the clinician may insert lead 18A into lead slot 66, and may mechanically and electrically couple the proximal contacts of lead 18 to respective lead connector contacts of outer housing 22 using one or more of the affixation mechanisms discussed above with respect to FIG. 5. The A-A line of FIG. 6 illustrates a side view of a plane that forms the basis of a cross-sectional view of outer housing 22 that is described below with respect to FIG. 7.

Figure 7:
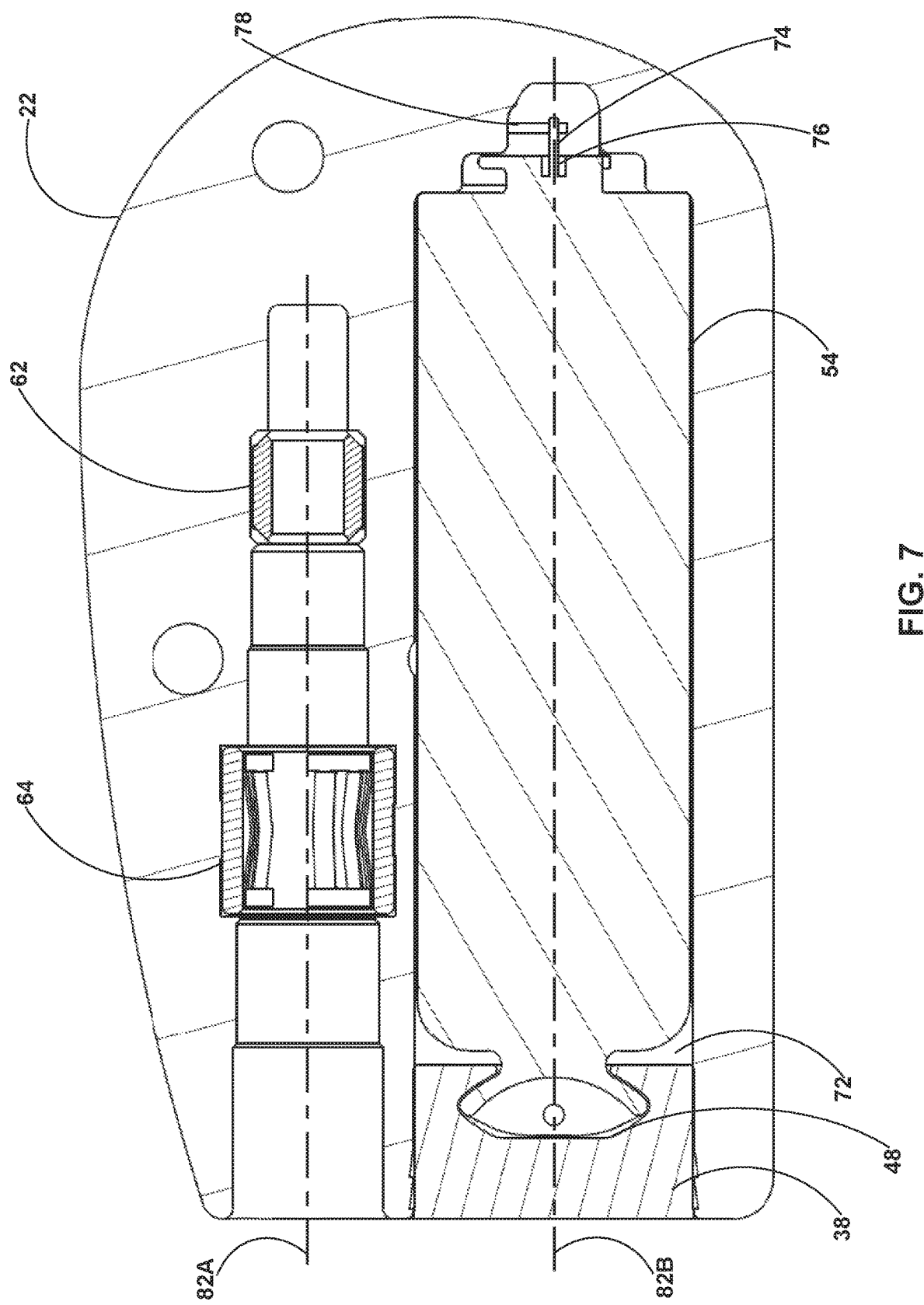
FIG. 7 is a conceptual diagram illustrating a longitudinal cross-sectional view of the outer housing of the IMD of this disclosure.

FIG. 7 is a conceptual diagram illustrating a longitudinal cross-sectional view of outer housing 22. In the example of FIG. 7, inner housing 54 is already inserted into chamber 72 and affixed to the outer rim of chamber 72. Also, in the example of FIG. 7, IMD 34 is configured for bipolar pacing and sensing, as shown by the presence of plug 38 at the proximal end of chamber 72. As described above, the body of inner housing is electrically conductive.

The cross-sectional view of inner housing 54 shown in FIG. 7 illustrates feedthrough pin 74. Feedthrough pin 74 is electrically conductive, and is set to the opposite polarity of the body of inner housing 54. To avoid short circuiting, feedthrough pin 74 is insulated from the rest of inner housing 54 by insulative sheath 76. A cross section of insulative sheath 76 is shown in FIG. 7, and may be an open-ended, hollow cylinder or an open-ended, hollow elliptic cylinder. Insulative sheath 76 may be constructed of various types of insulative material such as, but not limited to, glass.

Internal contact 78 electrically connects feedthrough pin 74 to connector contact 62. In this way, internal contact 78 connects feedthrough pin 74, via connector contact 62, to a proximal contact of lead 18, when lead 18 is inserted into lead slot 66. For example, conduction path 58 of FIG. 5 may connect feedthrough pin 74 to connector contact 62. Again, the proximal contact of lead 18 that is affixed to connector contact 62 represents the lone contact of a unipolar implementation of lead 18, or represents one of two proximal contacts of a bipolar implementation of lead 18. Electronic circuitry positioned within inner housing 54 is coupled to both the body of inner housing 54 and to feedthrough pin 74. The electronic circuitry is configured to deliver electrical stimulation therapy (e.g., in the form of cardiac pacing signals) to patient 14 via inner housing 54 and feedthrough pin 74. In some examples, the electronic circuitry is configured to sense electrical signals of patient 14 (e.g., a cardiac signal put out by heart 12) via inner housing 54 and feedthrough pin 74.

Connector contact 64 may be coupled to the body of inner housing 54 via conduction path 68 illustrated in FIG. 5. In examples in which lead 18 is a bipolar lead, the second proximal contact of lead 18 is electrically coupled to the body of inner housing 54 via conduction path 68 and connector contact 64. In these examples, feedthrough pin 74 and the body of inner housing 54 enable bipolar pacing and/or sensing by way of their opposite polarities (and being insulated from each other by insulative sheath 76) via electrical communications with the proximal contacts of lead 18. In this way, outer housing 22 is constructed, according to aspects of this disclosure, to enable the electronic circuitry of inner housing 54 to drive bipolar pacing signals via conductive connections to connector contacts 62 and 64, and thereby, to the proximal bipolar contacts of lead 18.

In examples in which lead 18 is a unipolar lead, connector contact 64 contacts a non-conductive portion of lead 18, and conduction path 68 therefore does not conduct any electrical signals between connector contact 64 and the body of inner housing 54. In these examples, the clinician may remove plug 38, thereby exposing device electrode 48 to the conductive tissue and body fluid of patient 14. In these examples, feedthrough pin 74 and device electrode 48 enable unipolar pacing and/or sensing by way of their opposite polarities (and being insulated from each other by insulative sheath 76) via electrical communications with, respectively, the lone proximal contact of lead 18 and with a distal electrode of lead 18 via the conductive tissue and body fluid of patient 14.

It will be appreciated that device electrode 48 may be implemented in various ways, and is not limited to the example shown and discussed with respect to inner housing 54 in all instances. In some examples consistent with aspects of this disclosure, device electrode 48 may represent any conductive element coupled to housing 54 that may be exposed by removal of the removable portion (in some examples, plug 38) of outer housing 22. In this way, outer housing 22 is constructed, according to aspects of this disclosure, to enable the electronic circuitry of inner housing 54 to drive unipolar pacing signals via conductive connections to connector contact 62 and to a distal electrode of lead 18. In some examples, inner housing 54, feedthrough pin 74, insulative sheath 76, internal contact 78, and device electrode 48 may be included in a subassembly included in IMD 34.

FIG. 7 shows axis 82A and axis 82B (collectively, axes 82). Axes 82 illustrate that, in the particular implementation shown in FIG. 7, chamber 72 and lead slot 66 are parallel or at least substantially parallel to one another. As such, inner housing 54 and the portion of lead 18 that is contained within outer housing 22 are disposed at least substantially parallel to one another upon assembly of IMD 34. In other implementations in accordance with aspects of this disclosure, lead slot 66 and chamber 72 may be positioned differently from the manner shown in the non-limiting example of FIG. 7.

Figure 8:
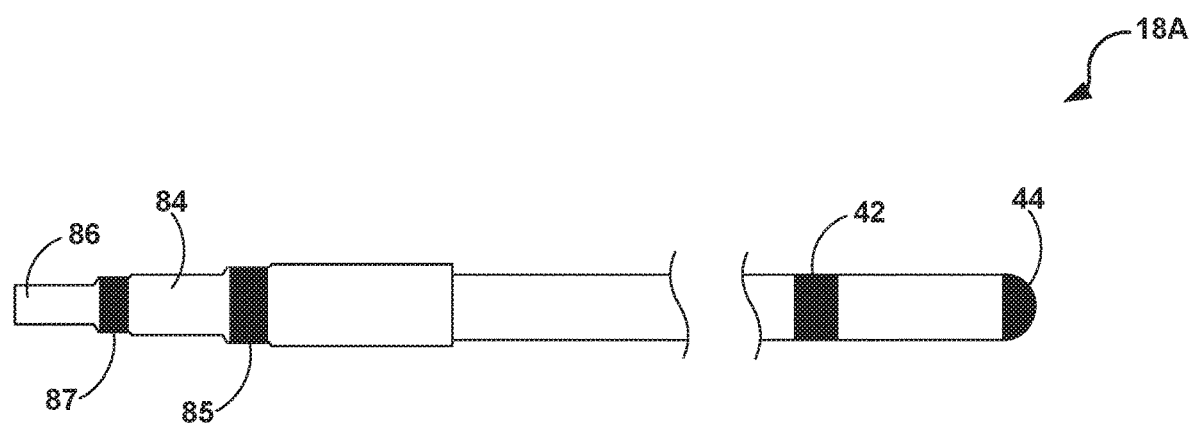
FIG. 8 is a conceptual diagram illustrating an example implementation of the bipolar pacing lead of FIG. 2A.

FIG. 8 is a conceptual diagram illustrating an example implementation of bipolar pacing lead 18A of FIG. 2A. Bipolar pacing lead 18A includes electrodes 42 and 44, which may be deployed to the target site for electrical stimulation delivery, such as to right ventricle 28 of heart 12. Of electrodes 42 and 44, one may be configured as the anode, and the other as the cathode, to complete a pacing circuit between electrodes 42 and 44.

Bipolar pacing lead 18A also includes proximal contacts 84 and 86, in the example shown in FIG. 8. Proximal contact 86 may be electrically and mechanically coupled to connector contact 62 of outer housing 22, upon the clinician affixing bipolar pacing lead 18A to outer housing 22 to construct IMD 34A of FIG. 2A. Proximal contact 84 may be electrically and mechanically coupled to connector contact 64 of outer housing 22, upon the clinician affixing bipolar pacing lead 18A to outer housing 22 to construct IMD 34A of FIG. 2A. Bipolar pacing lead 18A and/or the device port may also include seals 85 and 87. Seals 85 and 87 electrically isolate proximal contacts 84 and 86 within the connector, and deter/prevent fluid ingress that may interfere with the electrical pacing signals.

The electronic circuitry of inner housing 54 may drive pacing signals, through connector contacts 62 and 64, and thereby through proximal contacts 84 and 86 of bipolar pacing lead 18A, to deliver electrical stimulation therapy to right ventricle 28 via electrodes 42 and 44. In this way, outer housing 22 and bipolar pacing lead 18A are configured, according to aspects of this disclosure, to function synergistically to deliver bipolar pacing to heart 12. The clinician may affix bipolar pacing lead 18A to outer housing 22 during or immediately preceding the implantation procedure, if the clinician's evaluation results in a decision that bipolar pacing would better suit the present needs of patient 14.

Figure 9:
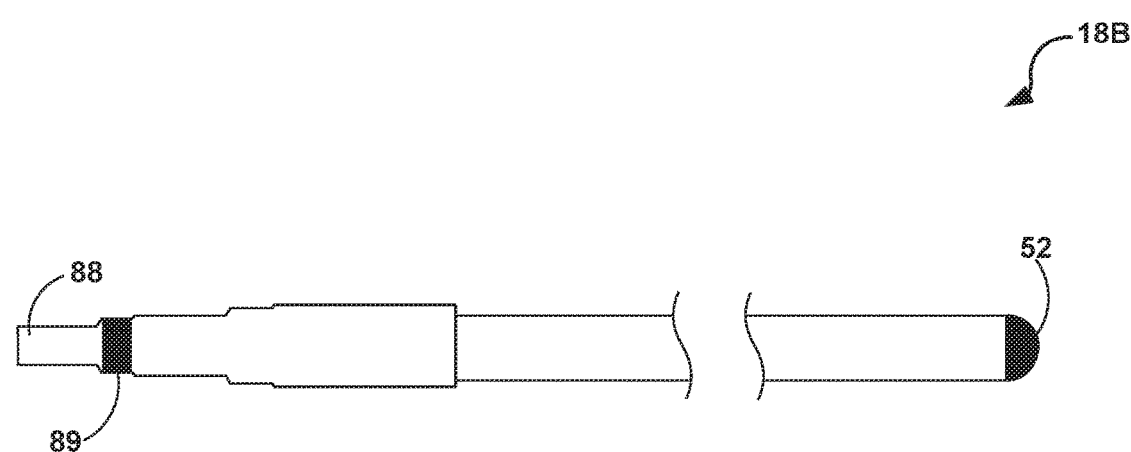
FIG. 9 is a conceptual diagram illustrating an example implementation of the unipolar pacing lead of FIG. 2B.

FIG. 9 is a conceptual diagram illustrating an example implementation of unipolar pacing lead 18B of FIG. 2B. Unipolar pacing lead 18B includes lead electrode 52, which may be deployed to the target site for electrical stimulation delivery, such as to right ventricle 28 of heart 12. Lead electrode 52 may be configured as the cathode of the unipolar pacing circuit, to complete a pacing circuit between lead electrodes 52 and device electrode 48, which may be configured to function as the anode of the unipolar pacing circuit.

Unipolar pacing lead 18B also includes proximal contact 88, in the example shown in FIG. 9. Proximal contact 88 may be electrically and mechanically coupled to connector contact 62 of outer housing 22, upon the clinician affixing unipolar pacing lead 18B to outer housing 22 to construct IMD 34B of FIG. 2B. A non-conductive portion of unipolar pacing lead 18B may be in contact with connector contact 64 of outer housing 22, upon the clinician affixing unipolar pacing lead 18B to outer housing 22 to construct IMD 34B of FIG. 2B. Uniplolar pacing lead 18B and/or the device port may also include seal 89. Seal 89 may electrically isolate proximal contact 88 within the connector, and may deter/prevent fluid ingress that may interfere with the electrical pacing signals.

The electronic circuitry of inner housing 54 may drive pacing signals, through connector contact 62, and thereby through proximal contact 88 of unipolar pacing lead 18A, to deliver electrical stimulation therapy to right ventricle 28 via device electrode 48 and lead electrode 52, with the electrically conductive tissue and body fluid of patient 14 enabling the completion of the unipolar pacing circuit.

In this way, outer housing 22 and unipolar pacing lead 18B are configured, according to aspects of this disclosure, to function synergistically to deliver unipolar pacing to heart 12. The clinician may affix unipolar pacing lead 18B to outer housing 22 during or immediately preceding the implantation procedure, if the clinician's evaluation results in a decision that unipolar pacing would better suit the present needs of patient 14. In some examples, two or more of outer housing 22, inner housing 54, plug 38, bipolar lead 18A, or unipolar lead 18B may be included in an IMD kit that the clinician can procure before an implantation procedure, for dynamic configuration at a later stage.

Figure 10:
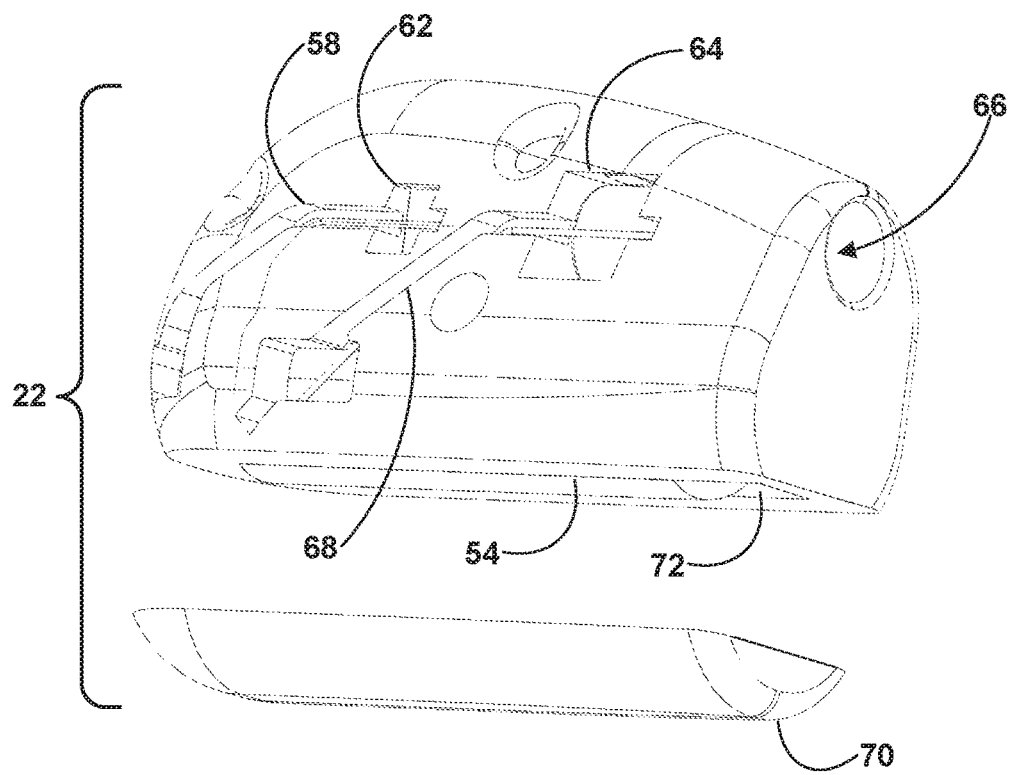
FIG. 10 is a conceptual diagram illustrating an exploded view of the outer housing at a pre-assembly phase of an alternate embodiment of the IMD of this disclosure, showing a removable cover.

FIG. 10 is a conceptual diagram illustrating an exploded view of outer housing 22 at a pre-assembly phase of an alternate embodiment of IMD 34, showing a removable cover. FIG. 10 shows the placement of inner housing within chamber 72, at a time when lead slot 66 is still left open and ready to receive lead 18. The pre-assembly phase of FIG. 10 is shown by the pre-insulated state of conduction paths 58 and 68. The embodiment of IMD 34 shown in FIG. 10 includes a removable portion 70 that the clinician can detach to access chamber 72. That is, the embodiment of IMD 34 shown in FIG. 10, the clinician may remove, or alternatively affix/leave in place removable portion 70 to configure IMD 34 for unipolar packing or bipolar pacing, respectively. Removable portion 70 provides functionality in the embodiment of FIG. 10 that is equivalent to the functionality provided by plug 38 illustrated in the embodiments shown in FIGS. 1-3, 6, and 7.

Figure 11:
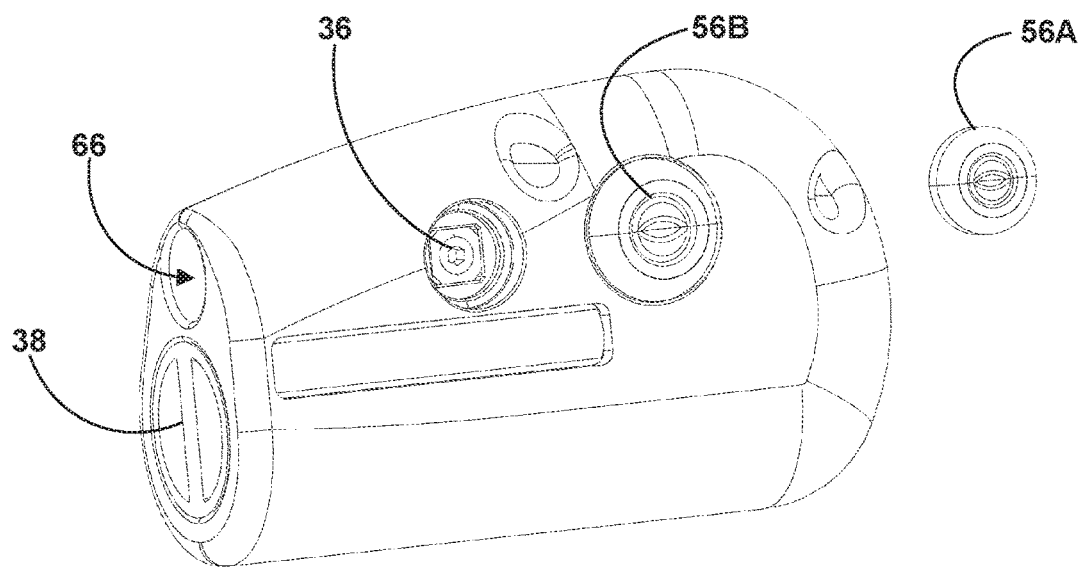
FIG. 11 is a conceptual diagram illustrating a profile view of a side of the outer housing of the IMD of this disclosure.

FIG. 11 is a conceptual diagram illustrating a profile view of a side of outer housing 22. FIG. 11 shows a view outer housing 22 that is on the opposite side with respect to FIGS. 3, 4, and 10. Set screw 36 is positioned opposite to connector contact 64, and the clinician may manipulate set screw 36 to connect a portion of lead 18 (whether a conductive or insulative portion) to connector contact. The clinician may affix insulative cap 56A over set screw 36 once lead 18 is affixed, to maintain the insulative property throughout the outer surface of outer housing 22. The clinician may remove insulative cap 56B from outer 22 housing 22 to gain access to another set screw positioned opposite to connector contact 62. Upon affixing lead 18, the clinician may re-affix insulative cap 56B over the other set screw, to maintain the insulative property throughout the outer surface of outer housing 22.

Figure 12:
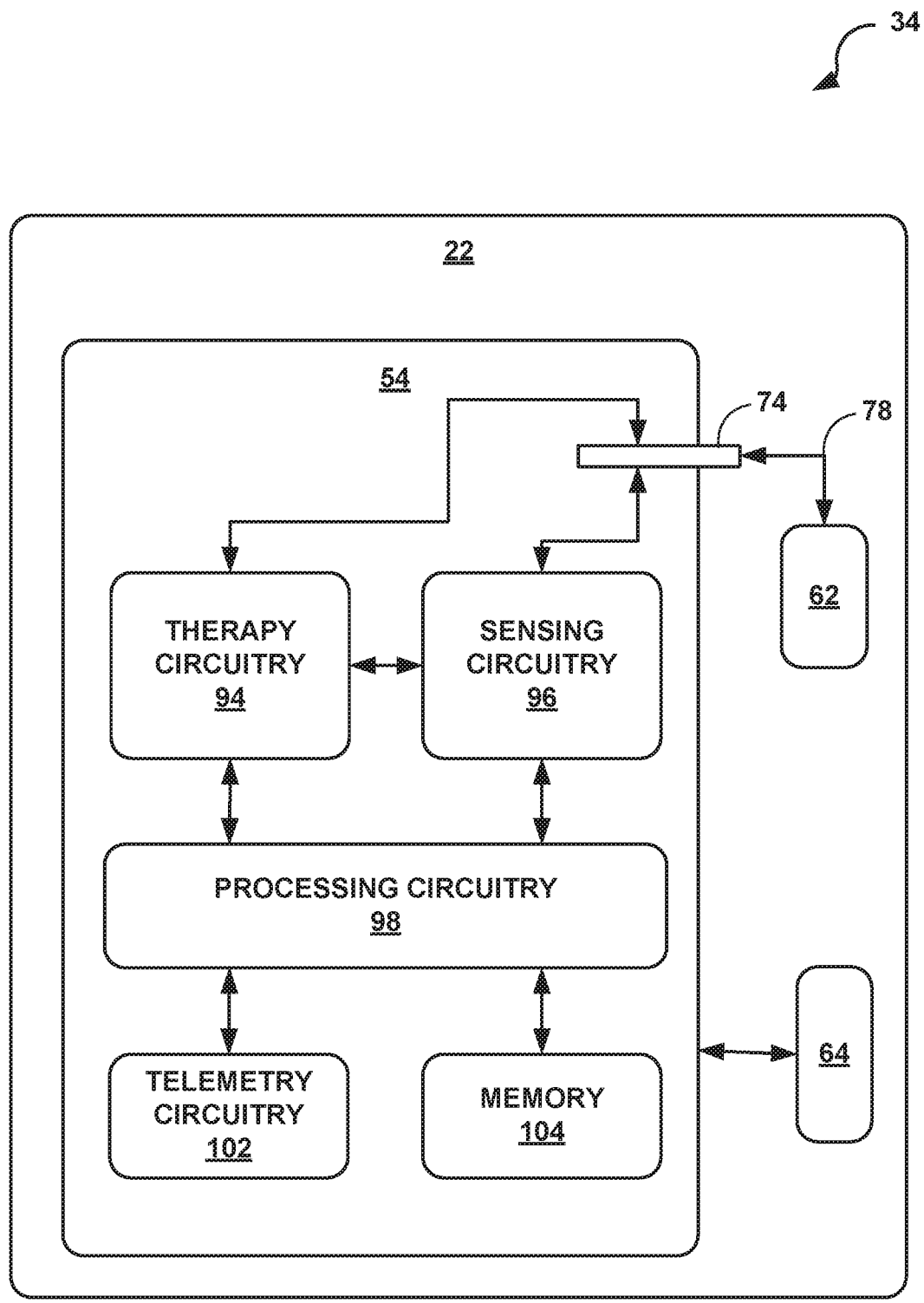
FIG. 12 is a block diagram of an example implementation of the IMD of this disclosure, in accordance with one or more aspects of this disclosure.

FIG. 12 is a block diagram of an example implementation of IMD 34, in accordance with one or more aspects of this disclosure. In the illustrated example, IMD 34 includes therapy circuitry 94, sensing circuitry 96, processing circuitry 98, telemetry circuitry 102, and memory 104 within conductive inner housing 54. Processing circuitry 98, memory 104, therapy circuitry 94, sensing circuitry 96, and/or telemetry circuitry 102 may be mounted on a circuit board of an electronics unit within conductive inner housing 54 of IMD 34.

Memory 104 may be encoded with computer-readable instructions that, when executed by processing circuitry 98, cause processing circuitry 98 to perform various functions of IMD 34 such as storing and analyzing signals received by IMD 34 and providing electrical stimulation therapy (such as in the form of pacing signals) to heart 12 of patient 14. Memory 104 may include any volatile, non-volatile, magnetic, optical, or electrical media, such as a random-access memory (RAM), read only memory (ROM), non-volatile RAM (NVRAM), electrically-erasable programmable ROM (EEPROM), flash memory, or any other digital or analog media.

Processing circuitry 98 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 98 may include multiple components, such as any combination of one or more microprocessors, one or more controllers, one or more DSPs, one or more ASICs, or one or more FPGAs, as well as other discrete or integrated logic circuitry. The functions attributed to processing circuitry 98 herein may be embodied as firmware, hardware, hardware implementing software, or any combination thereof. Processing circuitry 98 may represent programmable circuitry, fixed function circuitry, or any combination of programmable circuitry and/or fixed function circuitry.

Processing circuitry 98 controls therapy circuitry 94 to deliver electrical stimulation therapy to heart 12 of patient 14, according to therapy parameters, which may be stored in memory 104. For example, processing circuitry 98 may control therapy circuitry 94 to deliver electrical pulses with the amplitudes, pulse widths, frequency, or electrode polarities specified by the therapy parameters. In this manner, therapy circuitry 94 may deliver pacing pulses to right ventricle 28 (or other chamber) of heart 12 via a pair of electrodes, using connector contact 62 and a choice of either connector contact 64 or device electrode 48. IMD 34 may use any combination of electrodes (e.g., a combination of electrodes 42 and 44, or a combination of device electrode 48 with lead electrode 52) to deliver therapy and/or detect electrical signals from heart 12 of patient 14.

Therapy circuitry 94 is electrically coupled to connector contacts 62 and 64 of outer housing 22. In the illustrated example, therapy circuitry 94 is configured to generate and deliver electrical stimulation therapy to right ventricle 28 or other chamber of heart 12. For example, therapy circuitry 94 may deliver pulses to a portion of cardiac muscle within heart 12 via any combination of electrodes described above, depending on whether the clinician has configured IMD 34 for bipolar pacing or for unipolar pacing. In some examples, therapy circuitry 94 may deliver pacing stimulation in the form of electrical pulses. Therapy circuitry 94 may include charging circuitry, and one or more charge storage devices, such as one or more capacitors. Switching circuitry (not shown) may control when the capacitor(s) are discharged to the pair of electrodes being used presently.

Sensing circuitry 96 monitors signals from any of electrodes 42, 44, 48, or 52 to monitor electrical activity of heart 12, impedance, or another electrical phenomena. Sensing circuitry 96 may perform the sensing functionalities of this disclosure to determine heart rates or heart rate variability, or to detect arrhythmias (e.g., bradyarrhythmia or tachyarrhythmias) or other electrical signals. Sensing circuitry 96 may include switching circuitry to select the electrode polarity used to sense the heart activity. In some examples, processing circuitry 98 may select one or more particular electrodes to function as sensing electrodes, i.e., by selecting the sensing configuration via the switching circuitry of sensing circuitry 96.

Telemetry circuitry 102 includes any suitable hardware, firmware, or hardware implementing software, or any combination thereof for communicating with another device, such as an external device or another implantable device. In some examples, telemetry circuitry 102 may be configured for tissue conductive communication with another implantable medical device via any of electrodes 42, 44, 48, or 52. IMD 34 may communicate with an external device via the other implantable medical device, or telemetry circuitry 102 may be configured for radio-frequency communication with an external device, e.g., via an antenna.

Figure 13:
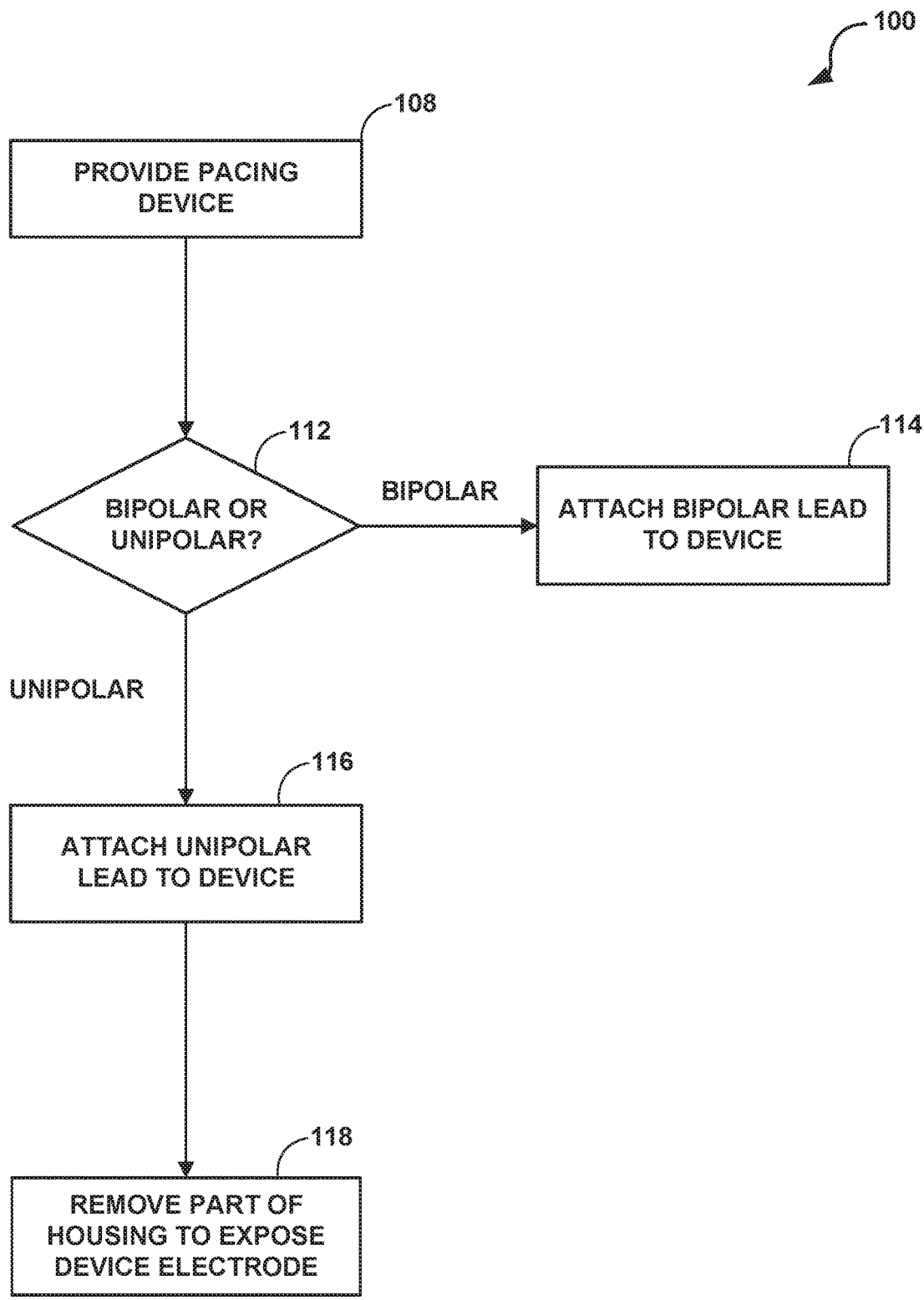
FIG. 13 is a flowchart illustrating an example process by which a clinician may dynamically configure the IMD of this disclosure for either bipolar or unipolar pacing by mechanical means, in accordance with aspects of this disclosure.

FIG. 13 is a flowchart illustrating an example process 100 by which a clinician may dynamically configure IMD 34 for either bipolar or unipolar pacing by mechanical means, in accordance with aspects of this disclosure. Process 100 may begin with the clinician providing a pacing device (108), such as by affixing inner housing 54 within chamber 72 of outer housing 22 and by affixing plug 38 to cover opening 46. In turn, the clinician may determine whether IMD 34 is to be configured for bipolar pacing/sensing or for unipolar pacing/sensing (decision block 112) based on various factors, such as the conditions observed or reported with respect to patient 14. If the clinician determines that IMD 34 should be configured for bipolar pacing (BIPOLAR branch of decision block 112), then the clinician may attach bipolar lead 18A to outer housing 22, such as via insertion into lead slot 66 (114). However, if the clinician determines that IMD 34 should be configured for unipolar pacing (UNIPOLAR branch of decision block 112), then the clinician may attach unipolar lead 18A to outer housing 22, such as via insertion into lead slot 66 (116). To complete the unipolar configuration (UNIPOLAR branch of decision block 112), the clinician may remove plug 38 from outer housing 22, thereby exposing device electrode 48 to the electrically conductive tissue and body fluids of patient 14 (118). In some examples, the clinician may procure two or more of outer housing 22, inner housing 54, plug 38, bipolar lead 18A, or unipolar lead 18B as an IMD kit before an implantation procedure, for dynamic configuration at a later time, such as during the performance of process 100 of FIG. 13.

The techniques described in this disclosure, including those attributed to IMD 34, computing device 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. An implantable medical device (IMD) comprising:
a first housing, the first housing being electrically conductive;
a feedthrough that extends through the first housing, the feedthrough being electrically conductive;
electronic circuitry positioned within the first housing, the electronic circuitry electrically coupled to the first housing and the feedthrough, the electronic circuitry being configured to at least one of: (i) sense electrical signals of a patient via the first housing and the feedthrough, or (ii) deliver electrical stimulation therapy to the patient via the first housing and the feedthrough;
a device electrode that either comprises a portion of the first housing or is electrically coupled to the first housing, the device electrode configured to electrically connect with at least one of tissue or a fluid at a target site in a patient; and
a second housing enclosing the first housing, the feedthrough, and the device electrode, the second housing comprising:
a lead connector configured to electrically connect to a proximal end of an implantable medical lead, the lead connector comprising a first connector contact electrically coupled to the feedthrough and a second connector contact electrically coupled to the first housing; and
a removable portion of the second housing that when present, covers the device electrode thereby enabling a bipolar pacing mode, and when removed, exposes the device electrode, thereby enabling a unipolar pacing mode.

2. The IMD of claim 1, wherein the second housing comprises an opening adjacent to the device electrode, and wherein the removable portion comprises a plug inserted into the opening.

3. The IMD of claim 2, wherein the plug is fastened within the opening with a friction fit.

4. The IMD of claim 2, wherein the plug is fastened within the opening with screw threads.

5. The IMD of claim 1, wherein the second housing comprises an opening adjacent the device electrode, and wherein the removable portion is adhered to an outer rim of the opening, thereby closing the opening.

6. The IMD of claim 1, wherein the electrically conductive first housing comprises the device electrode.

7. The IMD of claim 6, wherein the first housing is elongated with a proximal end and a distal end, wherein the feedthrough extends through the distal end of the first housing, and wherein the proximal end of the first housing comprises the device electrode.

8. The IMD of claim 1, wherein the second connector contact comprises a connector block and a set screw configured to mechanically and electrically connect to a proximal end of an implantable medical lead received within the opening of the lead connector, wherein the device electrode comprises at least one of the connector block or the set screw.

9. The IMD of claim 1, further comprising a conductive path that electrically couples the second connector contact with the electronic circuitry via the device housing, wherein the conductive path does not include a feedthrough.

10. The IMD of claim 1, wherein the opening in the second housing that forms the lead connector is the only opening in the second housing for connecting implantable medical leads.

11. An implantable medical device (IMD) comprising:
a subassembly comprising:
a first housing, the first housing being elongated, substantially sealed, and electrically conductive;
a feedthrough that extends through a distal end of the first housing, the feedthrough being electrically conductive; and
electronic circuitry within the first housing, the electronic circuitry electrically coupled to the first housing and the feedthrough, wherein the electronic circuitry is configured to at least one of sense electrical signals of a patient or deliver electrical stimulation therapy to the patient via the first housing and the feedthrough;
a device electrode that comprises at least a portion of the first housing or is electrically coupled to the first housing; and
a second housing enclosing the subassembly and the device electrode, the second housing comprising a removable portion and a lead connector configured to connect to a proximal end of an implantable medical lead, the lead connector comprising first and second connector contacts,
wherein the removable portion is configured to insulate the device electrode from at least one of a fluid or tissue at a target site in a patient by covering the device electrode when the removable portion is present, and
wherein the removable portion is configured to enable conduction between the device electrode and the at least one of the fluid or the tissue at the target site in the patient by exposing the device electrode when the removable portion is removed.

12. The IMD of claim 11, wherein the electronic circuitry is configured to provide a bipolar pacing mode and a unipolar pacing mode, wherein maintaining the removable portion covering the device electrode disables the unipolar pacing mode, and wherein removing the removable portion enables the unipolar pacing mode.

13. The IMD of claim 11, wherein the second housing comprises an opening adjacent the device electrode, and wherein the removable portion comprises a plug inserted into the opening.

14. The IMD of claim 13, wherein the plug is fastened within the opening with a friction fit.

15. The IMD of claim 13, wherein the plug is fastened within the opening with screw threads.

16. The IMD of claim 11, wherein the second housing comprises an opening adjacent the device electrode, and wherein the removable portion is adhered about the opening, thereby closing the opening.

17. The IMD of claim 11, wherein a proximal end of the first housing comprises the device electrode.

18. The IMD of claim 11, further comprising:
a first conductive path electrically coupling the first connector contact and the feedthrough; and
a second conductive path electrically coupling the second connector contact and the first housing,
wherein the first and the second conductive paths are contained within the second housing.

19. An implantable medical device kit, comprising:
an implantable medical device comprising:
a subassembly comprising:
a first housing, the first housing being elongated, substantially sealed, and electrically conductive;
a feedthrough electrically coupled to the electronic circuitry and extending through a distal end of the first housing;
electronic circuitry enclosed within and electrically coupled to the first housing, the electronic circuitry configured to at least one of generate an electrical stimulation therapy for delivery to a patient and monitor a physiological parameter of the patient; and
a device electrode electrically coupled to the electronic circuitry; and
a second housing enclosing the subassembly and the device electrode, the second housing comprising an opening adjacent the device electrode and comprising a lead connector configured to connect to a proximal end of an implantable medical lead, the lead connector comprising a first connector contact electrically coupled to the feedthrough and a second connector contact electrically coupled to the electronic circuitry; and
a removable plug configured to be inserted into the opening of the second housing;
wherein the removable plug is configured to insulate the device electrode from at least one of a fluid and tissue at a target site in a patient by covering the device electrode when the removable plug is inserted into the opening of the second housing, and
wherein the removable plug is configured to enable conduction between the device electrode and the at least one of the fluid or tissue at the target site in the patient by exposing the device electrode when the removable plug is removed from the opening of the second housing.

20. The implantable medical device kit of claim 19, further comprising at least one of a bipolar medical lead and a unipolar medical lead.

21. A method for configuring an implantable medical device prior to implantation in a patient, comprising:
making a pacing determination to provide one of bipolar pacing and unipolar pacing with an implantable medical device comprising:
electronic circuitry configured to provide a bipolar pacing mode and a unipolar pacing mode;
a first housing, the first housing being electrically conductive and electrically coupled to the electronic circuitry;
a feedthrough electrically coupled to the electronic circuitry and extending through the first housing;
a device electrode electrically coupled to the electronic circuitry; and
a second housing enclosing the first housing, the feedthrough, and the device electrode, the second housing comprising:
a first portion comprising an opening adjacent the device electrode;
a removable portion; and
a lead connector comprising a first connector contact electrically coupled to the feedthrough and a second connector contact electrically coupled to the electronic circuitry;
selecting one of a bipolar implantable medical lead or a unipolar implantable medical lead based on the pacing determination;
inserting a proximal end of the selected implantable medical lead into the lead connector; and
configuring the removable portion of the second housing based on the pacing determination.

22. The method of claim 21, wherein making the pacing determination comprises determining to provide bipolar pacing,
wherein the lead is a bipolar lead, and
wherein configuring the removable portion of the second housing comprises closing the opening with the removable portion to cover the device electrode.

23. The method of claim 22, wherein the implantable medical device is provided with the removable portion separate from the first portion of the second housing and wherein closing the opening comprises plugging the opening with the removable portion, thereby covering the device electrode.

24. The method of claim 22, wherein the implantable medical device is provided with the removable portion fastened to the first portion of the second housing and wherein closing the first opening comprises keeping the removable portion fastened to the first portion, thereby covering the device electrode.

25. The method of claim 21, wherein making the pacing determination comprises determining to provide unipolar pacing,
wherein the lead is a unipolar lead, and
wherein configuring the removable portion of the second housing comprises removing the removable portion from the first portion of the second housing to expose the device electrode through the opening.

26. The method of claim 21, wherein making the pacing determination comprises determining to provide unipolar pacing,
wherein the lead is a unipolar lead,
wherein the implantable medical device is provided with the removable portion separate from the first portion of the second housing and the device electrode exposed through the opening, and
wherein configuring the removable portion of the second housing comprises not closing the opening with the removable portion, thereby continuing to expose the device electrode through the opening.

* * * * *